US008452716B2

(12) United States Patent
Howley et al.

(10) Patent No.: US 8,452,716 B2
(45) Date of Patent: May 28, 2013

(54) KERNEL-BASED METHOD AND APPARATUS FOR CLASSIFYING MATERIALS OR CHEMICALS AND FOR QUANTIFYING THE PROPERTIES OF MATERIALS OR CHEMICALS IN MIXTURES USING SPECTROSCOPIC DATA

(76) Inventors: Tom Howley, Galway (IE); Alan George Ryder, Galway (IE); Michael Gerard Madden, Galway (IE); Kenneth Hennessy, Galway (IE)

( * ) Notice: Subject to any disclaimer, the term of this patent is extended or adjusted under 35 U.S.C. 154(b) by 648 days.

(21) Appl. No.: 12/595,023

(22) PCT Filed: May 16, 2008

(86) PCT No.: PCT/EP2008/056078
§ 371 (c)(1),
(2), (4) Date: Mar. 10, 2010

(87) PCT Pub. No.: WO2008/138996
PCT Pub. Date: Nov. 20, 2008

(65) Prior Publication Data
US 2010/0179934 A1 Jul. 15, 2010

(30) Foreign Application Priority Data
May 16, 2007 (EP) .................................... 07108394

(51) Int. Cl.
*G06F 15/18* (2006.01)
(52) U.S. Cl.
USPC ............................................................. 706/12
(58) Field of Classification Search
USPC ............................................................. 706/12
See application file for complete search history.

(56) References Cited

U.S. PATENT DOCUMENTS

| 5,424,959 | A | * | 6/1995 | Reyes et al. | 702/28 |
| 6,326,140 | B1 | * | 12/2001 | Rine et al. | 435/6.12 |
| 7,283,684 | B1 | * | 10/2007 | Keenan | 382/276 |
| 2005/0228591 | A1 | | 10/2005 | Hur et al. | |

OTHER PUBLICATIONS

Goodacre, Royston et al "Rapid Identification of Urinary Tract infection bacteria using hyperspectral whole-organism fingerprinting and artificial neural networks" Microbiologoy 1998. [Online] Downloaded Aug. 2, 2012http://mic.sgmjournals.org/content/144/5/1157.full.pdf.*

(Continued)

*Primary Examiner* — Ben Rifkin
(74) *Attorney, Agent, or Firm* — Loza & Loza LLP; Anthony G. Smyth

(57) ABSTRACT

A kernel-based method determines the similarity of a first spectrum and a second spectrum. Each spectrum represents a result of spectral analysis of a material or chemical and comprises a set of spectral attributes distributed across a spectral range. The method calculates a kernel function which makes use of the shape of the spectral response surrounding a spectral point. This is achieved by comparing the value of an spectral attribute in a spectrum and each of a set of neighboring spectral attributes within a window around the spectral attribute. Weighting values can be applied to calculations when deriving the kernel function. The weighting values can assign different degrees of importance to different regions of the spectrum. The method can be used to: classify unknown spectra; predict the concentration of an analyte within a mixture; database searching for the closest match using a kernel-derived distance metric; visualization of high-dimensional spectral data in two or three dimensions.

26 Claims, 8 Drawing Sheets

OTHER PUBLICATIONS

Beyssac, Oliver et al "On the Characterization of disordered and heterogeneous carbonacous materials by Ramn Spectroscopy" Spectrochomica Acta Part A, 2003 [Online] Downloaded Aug. 5, 2012.*

O'Connell et al., Classification of a target analyte in solid mixtures using principal component analysis, support vector machines, and Raman spectroscopy, Proceedings of the Spie, Spie, Bellingham, VA, US, vol. 5826 (No. 1), 2005, pp. 340-350.

Nicolai et al., Kernel PLS regression on wavelet transformed NIR spectra for prediction of sugar content of apple, Chemometrics and Intelligent Laboratory Systems, Elsevier Science Publishers B.V. Amsterdam, NL, vol. 85 (No. 2), Feb. 2007, pp. 243-252.

Langeron et al., Classifying NIR spectra of textile products with kernel methods, Engineering Applications of Artificial Intelligence, Pineridge Press, Swansea, GB, vol. 20 (No. 3), Mar. 2007, pp. 415-427.

Howley et al., The effect of principal component analysis on machine learning accuracy with high-dimensional spectral data, Knowledge-Based Systems, Elsevier, vol. 19 (No. 5), Sep. 2006, pp. 363-370.

International Search Report, PCT/EP2008/056078, Jun. 10, 2008.

* cited by examiner

KERNEL-BASED METHOD AND APPARATUS FOR CLASSIFYING MATERIALS OR CHEMICALS AND FOR QUANTIFYING THE PROPERTIES OF MATERIALS OR CHEMICALS IN MIXTURES USING SPECTROSCOPIC DATA

This Application is a National Stage Application of, and claims priority from, PCT Application Number PCT/EP2008/056078, filed May 16, 2008, which is hereby incorporated by reference herein for all purposes.

FIELD OF THE INVENTION

The present invention relates to the quantitative and qualitative analysis of materials or chemicals based on machine learning analysis of spectroscopic data. The term 'spectroscopic data' here includes data collected from techniques based on: Infra-Red (IR) absorption; Raman scattering; Near-Infra-Red (NIR) absorption; Fluorescence emission; and Nuclear Magnetic Resonance (NMR).

BACKGROUND TO THE INVENTION

An application of this invention to spectroscopic data involves its use in Raman spectroscopy.

Raman spectroscopy has historically been used to obtain vibrational spectroscopic data from a large number of chemical systems. Its versatility, due to ease of sampling via coupling to fibre optics and microscopes, allied to the ability to sample through glass or plastic, has made it a very practical technique for use by law enforcement agencies in the detection of illicit materials. It also has the highly desirable properties of being non-invasive, non-destructive and very often highly selective. The analytical applications of Raman Spectroscopy continue to grow and typical applications are in structure determination, multi-component qualitative analysis and quantitative analysis.

The Raman spectrum of an analyte (i.e. a substance or chemical constituent that is undergoing analysis) may be compared against reference spectra of known substances to identify the presence of the analyte. For more complex (or poorly resolved) spectra, the process of identification is more difficult. The current norm is to develop test sets of known samples and use chemometric methods such as Principal Component Analysis (PCA) and multivariate regression to produce statistical models to classify and/or quantify the analyte from the spectroscopic data. These statistical based models are however, limited in performance for complex systems that have poorly resolved peaks and/or comprise complex mixtures.

Recent advances in machine learning have led to new techniques capable of outperforming these chemometric methods. Machine Learning techniques are more robust and therefore more capable of overcoming the above-mentioned problems. These techniques have been successfully employed in the past to identify and quantify compounds based on other forms of spectroscopic data, such as the use of artificial neural networks (ANNs) to identify bacteria from their IR Spectra and the use of ANNs to classify plant extracts from their mass spectra. A more recent machine learning method is the kernel-based Support Vector Machine (SVM), a powerful classification and regression tool, which is also suited to handling the problems encountered in the spectral analysis of complex mixtures.

There are very few machine learning packages on the market that are specifically dedicated to analysing spectra. Gmax-bio (Aber Genomic Computing) is an application that is designed for use in many scientific areas including spectroscopy. Gmax-bio uses genetic programming to evolve solutions to problems and is claimed by its developers to outperform most other machine learning techniques. However, due to its diverse problem applicability, the user requires some prior knowledge of both genetic programming and spectroscopy. Neurodeveloper (Synthon GmBH), an application designed specifically for spectral analysis, uses standard chemometric tools, pre-processing techniques and also uses ANNs for the deconvolution of spectra.

There follows a discussion of prior art related to the present invention. U.S. Pat. No. 5,649,068 describes the Support Vector Machine. The SVM maps a set of training patterns to a kernel-defined space (a linear function corresponds to the original input space) and finds a linear decision surface in this space that realizes the maximum margin of separation between the two classes of samples in the training set. The decision surface is defined by a set of weights, each of which is associated with a training pattern, and the goal of the SVM training process is to find the set of weights that results in optimum separation of the two classes of data. During the SVM training process, training patterns or kernel-transformed training patterns that are unused to determine the decision function, are identified and removed to allow the training process to continue with the remaining training patterns. Those training patterns that remain in the final decision function are known as support vectors. The use of a relatively small set of support vectors (compared to training set size) results in a more computationally efficient method than previous maximum margin separation methods. A pre-cursor to the SVM patent is the Soft Margin Classifier (U.S. Pat. No. 5,640,492), which incorporates the use of slack variables that allow erroneous or difficult training patterns to be taken into account in the determination of the optimal hyperplane. As the SVM is a kernel method, i.e. is based on an underlying kernel function, the SVM invention can be used in combination with the WS Kernel invention described here. The WS Kernel improves the performance of SVMs in the classification of materials or chemicals and the quantification of properties of materials or chemicals based on spectroscopic data. Another SVM related system is described in U.S. Pat. No. 6,427,141, which discloses a system for enhancing knowledge discovery using multiple support vector machines.

Another example of a kernel method that can be used in conjunction with the WS Kernel invention is the k-Nearest Neighbour classification/regression technique. This well-known technique has been used in many previous patents, including: U.S. Pat. No. 6,592,033 (Item recognition method and apparatus), U.S. Pat. No. 6,011,990 (Method and device for evaluating an EEG carried out in the context of anaesthesia or intensive care) and U.S. Pat. No. 6,198,846 (Character recognition system).

A number of patents have been published that disclose techniques, designed specifically for spectral analysis. As mentioned previously, PCA is widely used in the field of chemometrics; U.S. Pat. Nos. 6,675,137 and 5,822,219 disclose the use of PCA for spectral analysis. The use of other chemometric techniques, Partial Least Squares, classical least squares techniques, and hybrids of these, have been disclosed in U.S. Pat. Nos. 6,415,233, 6,711,503 and 6,096,533. Other approaches are based on the use of spectral pre-processing techniques, such as those described in U.S. Pat. No. 4,783,754, U.S. Pat. No. 5,311,445, U.S. Pat. No. 5,435,309, U.S. Pat. No. 5,652,653, U.S. Pat. No. 6,683,455 and U.S. Pat. No. 6,754,543. There is a need to provide a prediction method that is robust to noise, removing the need for such spectral pre-processing techniques.

Patents have also been published that disclose systems designed for the detection or quantification of a specific category of analytes, e.g. U.S. Pat. No. 6,762,060, which describes an apparatus and set of methods for monitoring the concentration of hazardous airborne substances, such as lead.

In the field of machine learning, the ANN is the most popular technique used for the spectral analysis, e.g. U.S. Pat. Nos. 5,631,469, 5,553,616 5,660,181 (which uses PCA in combination with PCA) 5,900,634, 5,218,529, 6,135,965 and 6,477,516. A limitation of existing techniques based on the ANN is that they produce predictions that are not particularly amenable to interpretation, due to the 'black box' nature of the ANN technique. This is in stark contrast to the situation in which a domain expert (e.g. analytical chemist or forensic scientist) manually inspects spectra and classifies them based on the position and size peaks. Naturally, this approach is not feasible for the scenarios targeted by this invention, the analysis of complex mixtures in particular. As such, domain experts using machine learning methods are typically at a disadvantage in that they are provided with no insight into the classification or quantification models used, or the data under analysis.

Another method for classifying spectra is disclosed in U.S. Pat. No. 6,421,553. This system uses a k-NN style classification technique and is based on the distance of an unknown sample from set of training samples (of known condition). The unknown sample is classified based on a distance relationship with at least two samples, provided that at least one distance is less than a predetermined maximum distance.

In addition to the ANN, there are many machine learning techniques that could be used for the analysis of spectra, such as those for classification (Decision Trees, Naïve Bayes, etc.) and techniques for regression (Model Trees, Least Median Squares, etc.). Kernel-based learning algorithms (such as the SVM for classification and for regression) present a unified approach to all the problems of classification, regression, clustering and can also be used in database search applications. The SVM is a machine learning technique that is suited to handling noisy data and is also suited to the high dimensionality that is characteristic of spectral data. However, as with the ANN, they are typically deployed in a way that does not provide experts with added insight.

Furthermore, kernel methods have not been tailored specifically for spectral data, as has been done in other application domains, e.g. the string kernel for text classification. A key component of all kernel methods is the kernel, which acts as a similarity measure for comparing two objects of a dataset that is being used to build a prediction model. In the problem domain of this invention, the kernel compares two sample spectra and returns a value that indicates how similar they are; the higher this value, the more similar they are. The way in which this similarity measure or kernel is used to build a prediction model differs between kernel methods. For example, k-NN uses the kernel to derive a distance metric, i.e. to measure the distance between two data samples. When applied to spectral data, a conventional kernel considers each spectral point in isolation, i.e. for each spectral point where a calculation is performed, e.g. the dot-product calculation of the Linear kernel or the Euclidean distance calculation of the RBF kernel, the kernel operates on just that spectral point in the two samples being compared.

OBJECT OF THE INVENTION

The present invention seeks to provide a method and apparatus capable of increasing the clarity and accuracy of kernel method-based materials and chemicals classification and quantification decisions, which can be used with Raman spectral analysis or other spectroscopic techniques.

SUMMARY OF THE INVENTION

A first aspect of the present invention provides a method of determining the similarity of a first spectrum and a second spectrum, each spectrum representing a result of spectral analysis of a material or chemical, each spectrum comprising a set of m spectral attributes distributed across a spectral range, the method comprising calculating a kernel function which comprises:

(a) calculating a value representing the similarity of the two spectra at an $i^{th}$ one of the spectral attributes;
(b) repeating the above calculation for each of the set of m spectral attributes;
(c) combining the results of the m calculations to derive a value indicative of the similarity of the two spectra, and wherein step (a) comprises:

comparing the value of the $i^{th}$ spectral attribute in the first spectrum and each of a set of neighbouring spectral attributes within a window around the $i^{th}$ spectral attribute in the first spectrum; and comparing the value of the $i^{th}$ spectral attribute in the second spectrum and each of a set of neighbouring spectral attributes within a window around the $i^{th}$ spectral attribute in the second spectrum;

wherein the windows in the first and second spectrum are the same size.

This method has an advantage that points on a spectrum (i.e. values of spectral attributes) are considered within the context of other points in the neighbourhood surrounding them. In effect, the shape of the spectral response surrounding a spectral point is considered when the kernel operates on each spectral point. This exploits the linear structure of the spectrum, rather than treating points in isolation from each other. This improves accuracy over a conventional kernel technique which only looks for the similarity in the value of a single spectral point at each of a number of points spaced along the spectral response. The method can be applied to Linear, Radial Base Function (RBF) or other types of kernel function such as polynomial or Sigmoid kernels.

Advantageously, the window is symmetrical about the $i^{th}$ spectral attribute, although asymmetrical windows can also be used.

Preferably, the method calculates a single value which represents the similarity of the two spectra. The precise detail of the steps of the method differ between implementations of the method (e.g. Linear or Radial Base Function) and these are set out in the detailed description and accompanying claims.

In a preferred embodiment of the method, weighting values are used in the calculations. When comparing any two sample spectra, the spectrum of the analyte in its pure form is used to assign different degrees of importance (i.e. weightings) to different regions of the spectrum. Typically, a pure sample of any given analyte is readily available for reference purposes. This improvement is referred to as a 'Weighted Spectral Kernel' (abbreviated as WS Kernel) in the following description.

The invention further provides a method of determining the similarity of a first spectrum and a second spectrum, each spectrum representing a result of spectral analysis of a material or chemical, each spectrum comprising a set of m spectral attributes distributed across a spectral range, the method comprising calculating a kernel function which comprises:

(a) calculating a value representing the similarity of the two spectra at an $i^{th}$ one of the spectral attributes;

(b) repeating the above calculation for each of the set of m spectral attributes;

(c) adding the results of the m calculations to derive a value indicative of the similarity of the two spectra, and wherein step (a) comprises:

(ii) calculating the difference between the value of the $i^{th}$ spectral attribute in the first spectrum and each of a set of neighbouring spectral attributes within a window around the $i^{th}$ spectral attribute in the first spectrum;

(iii) calculating the difference between the value of the $i^{th}$ spectral attribute in the second spectrum and each of a set of neighbouring spectral attributes within a window around the $i^{th}$ spectral attribute in the second spectrum, wherein the windows in steps (i) and (ii) are the same size.

Step (a) may further comprise: multiplying the value of the $i^{th}$ spectral attributes in the first and second spectra and adding to same the output of a function which combines the results of steps (i) and (ii).

The value at step (a) may further be based on multiplying a difference calculated in step (i) with a corresponding difference calculated in step (ii), and summing each pair of calculated differences.

The present invention further provides a method of determining the similarity of a first spectrum and a second spectrum, each spectrum representing a result of spectral analysis of a material or chemical, each spectrum comprising a set of m spectral attributes distributed across a spectral range, the method comprising calculating a kernel function which comprises:

(a) calculating a value representing the similarity of the two spectra at an $i^{th}$ one of the spectral attributes;

(b) applying a weighting value to each of the calculations in step (a);

(c) repeating steps (a) and (b) for each of the set of m spectral attributes;

(d) deriving a value indicative of the similarity of the two spectra by adding the m calculations and negating the sum, dividing the result by an appropriate quantity, and calculating the exponential of this result, and wherein step (a) comprises:

(i) calculating the difference between the value of the $i^{th}$ spectral attribute in the first spectrum and each of a set of neighbouring spectral attributes within a window around the $i^{th}$ spectral attribute in the first spectrum;

(ii) calculating the difference between the value of the $i^{th}$ spectral attribute in the second spectrum and each of a set of neighbouring spectral attributes within a window around the $i^{th}$ spectral attribute in the second spectrum, wherein the windows in steps (i) and (ii) are the same size.

There may also be a third spectrum comprising a set of m spectral attributes distributed across the spectral range, the third spectrum representing a target analyte, and the value at step (a) may be further based on:

(iv) calculating the difference between the value of the $i^{th}$ spectral attribute in the third spectrum and each of a set of neighbouring spectral attributes within a window around the $i^{th}$ spectral attribute in the third spectrum and using each of the calculated differences for the third spectrum as a weighting value.

The value of step (a) may be further calculated by:

(d) subtracting the first difference for the second spectrum from the first difference for the first spectrum, squaring the result and multiplying this result by the first difference in the third spectrum;

(e) repeating the above step for each difference within the window;

(f) adding all the results produced by all iterations of step (d).

(g) multiplying the final sum by the value of the $i^{th}$ spectral attribute in the third spectrum Step (i) may comprise multiplying the squared difference by the value of $i^{th}$ spectral attribute in the third spectrum.

Step (a) may further comprise (iii) squaring the difference between the value of the $i^{th}$ spectral attribute in the first and second spectra and adding the output of step (iii) and the output of step (g).

The present invention further comprises a method of determining the similarity of a first spectrum and a second spectrum, each spectrum representing a result of spectral analysis of a material or chemical, each spectrum comprising a set of m spectral attributes distributed across a spectral range, the method comprising calculating a kernel function which comprises:

(a) calculating a value representing the similarity of the two spectra at an $i^{th}$ one of the spectral attributes;

(b) applying a weighting value to each of the calculations in step (a).

(c) repeating steps (a) and (b) for each of the set of m spectral attributes;

(d) summing the results of the m calculations to derive a value indicative of the similarity of the two spectra, and wherein step (a) comprises:

(i) calculating the difference between the value of the $i^{th}$ spectral attribute in the first spectrum and each of a set of neighbouring spectral attributes within a window around the $i^{th}$ spectral attribute in the first spectrum;

(ii) calculating the difference between the value of the $i^{th}$ spectral attribute in the second spectrum and each of a set of neighbouring spectral attributes within a window around the $i^{th}$ spectral attribute in the second spectrum, wherein the windows in steps (i) and (ii) are the same size.

A weighting value may be applied to each of the difference calculations in steps (i) and (ii).

There may be a third spectrum comprising a set of m spectral attributes distributed across the spectral range, the third spectrum representing a target analyte, and the value at step (a) may be further based on:

(iii) calculating the difference between the value of the $i^{th}$ spectral attribute in the third spectrum and each of a set of neighbouring spectral attributes within a window around the $i^{th}$ spectral attribute in the third spectrum and using each of the calculated differences for the third spectrum as a weighting value.

The value at step (a) may be based on:

multiplying a difference calculated in each of steps (i), (ii) and (iii) for a particular spectral attribute within the window;

summing the results of the set of difference calculations;

multiplying the summed result by the spectral attribute in the third spectrum.

The method may further comprise multiplying the spectral attribute in the first spectrum, the second spectrum and the third spectrum.

Step (a) may further comprise multiplying the value of the $i^{th}$ spectral attributes in the first and second spectra and adding same to the output of Claim 15.

The method may further comprise normalising the third spectrum so that all of the spectral attributes of the third spectrum lie in the range of 0 to 1.

According to a further aspect of the invention, there is provided a method of determining the similarity of a first spectrum and a second spectrum, each spectrum representing a result of spectral analysis of a material or chemical, each spectrum comprising a set of in spectral attributes distributed across a spectral range, the method comprising calculating a kernel function which comprises:
  (a) calculating a value representing the similarity of the two spectra at an $i^{th}$ one of the spectral attributes;
  (b) repeating the above calculation for each of the set of m spectral attributes;
  (c) combining the results of the in calculations to derive a value indicative of the similarity of the two spectra,
and wherein the value at step (a) is based on:
  (i) combining the value of the $i^{th}$ spectral attributes in the first and second spectra;
  (ii) calculating the difference between the value of the $i^{th}$ spectral attribute in the first spectrum and each of a set of neighbouring spectral attributes within a window around the $i^{th}$ spectral attribute in the first spectrum;
  (iii) calculating the difference between the value of the $i^{th}$ spectral attribute in the second spectrum and each of a set of neighbouring spectral attributes within a window around the $i^{th}$ spectral attribute in the second spectrum.

Step (c) may comprise adding the results of the m calculations. The value at step (a) may be further based on adding the output of step (i) and the output of a function which combines the results of steps (ii) and (iii).

The value at step (a) may be further based on multiplying a difference calculated in step (ii) with a corresponding difference calculated in step (iii), and summing each pair of calculated differences. Step (i) may comprise multiplying the value of the spectral attribute in the first spectrum and the second spectrum. Step (c) may comprise adding the m calculations and negating the sum, dividing the result by $2\sigma^2$, and calculating the exponential of this result. Step (i) may comprise squaring the difference between the value of the spectral attribute in the first and second spectrum.

The value of step (a) may be further calculated by:
  (d) subtracting the first difference for the second spectrum from the first difference for the first spectrum, squaring the result;
  (e) repeating the above step for each difference within the window;
  (f) adding all the results produced by all iterations of step (d).

The method may further comprising applying a weighting value to each of the calculations in step (a). A weighting value may be applied to each of the difference calculations in steps (ii) and (iii). There may be a third spectrum comprising a set of in spectral attributes distributed across the spectral range, the third spectrum representing a target analyte, and the value at step (a) may be further based on:
  (iv) calculating the difference between the value of the $i^{th}$ spectral attribute in the third spectrum and each of a set of neighbouring spectral attributes within a window around the $i^{th}$ spectral attribute in the third spectrum and using each of the calculated differences for the third spectrum as a weighting value.

The value at step (a) may be based on:
  multiplying a difference calculated in each of steps (ii), (iii) and (iv) for a particular spectral attribute within the window;
  summing the results of the set of difference calculations;
  multiplying the summed result by the spectral attribute in the third spectrum.

Step (i) may comprise multiplying the spectral attribute in the first spectrum, the second spectrum and the third spectrum. The method may further comprise normalising the third spectrum so that all of the spectral attributes of the third spectrum lie in the range of 0 to 1.

Step (i) may comprise squaring the difference between the value of the spectral attribute in the first and second spectrum, and multiplying this result by the value of the same spectral attribute in the third spectrum.

The value of step (a) may be further calculated by:
  (d) subtracting the first difference for the second spectrum from the first difference for the first spectrum, squaring the result and multiplying this result by the first difference for the third spectrum;
  (e) repeating the above step for each difference within the window;
  (f) adding all the results produced by all iterations of step (d) and multiplying this sum by the value of the spectral attribute in the third spectrum.

Preferred features of using this invention can be summarised as follows:

The presence of materials or chemicals in a mixture is detected by first building a classification model on a training set of spectra of samples of known composition, using a kernel-based classification technique that incorporates a WS kernel. The WS kernel-based classification model is then used to classify the spectrum of an unidentified sample.

Properties of a mixture are quantified by first building a regression model on a training set of spectra of samples, in which the desired properties of each sample are known, using a kernel-based regression technique that incorporates a WS kernel. For example, when using this invention to predict the concentration of analytes in a mixture, the training set comprises the spectra of samples of known composition. The WS-kernel based regression model is then used to quantify a particular property (such as the concentration of a particular analyte) of an unidentified sample based on the spectrum of that sample.

In the building of WS kernel-based classification or regression models, parameters of the kernel method and WS kernel itself may be optimised for a training set, e.g. by selecting parameter values that result in the best accuracy on that set. To generate a visualisation of a spectral dataset, the best WS kernel setting for that dataset is used to generate a matrix comprising the similarities of all pairs of spectra in the dataset. A multidimensional scaling (MDS) technique, e.g. Principal Component Analysis, is applied to the matrix in order to plot each spectrum in two or three dimensions. This allows the visualisation of the entire dataset and the uncovering of clusters of data samples. The visualisation can also serve to validate the underlying classification or regression model, e.g. by determining how well a classification model separates target samples from non-target samples.

A similar process of selecting the best WS kernel setting for a training dataset is carried out to generate a distance metric for spectra. The WS kernel-based distance metric is then used to calculate the distance between two spectra. Such a distance measure can be used in database search applications.

This approach facilitates the construction of a custom kernel for every analyte to be considered. The custom kernel can then be used for the following tasks:
1. Kernel-based classification of unknown spectra.
2. Kernel-based regression analysis for predicting the concentration of an analyte within a mixture.
3. Database searching for the closest match using a kernel-derived distance metric.
4. Visualisation of high-dimensional spectral data in two or three dimensions, using the kernel in combination with a specific transformation technique, such as kernel PCA.

Further aspects of the present invention relate to each of the above tasks.

The functionality of this invention can be implemented in software, hardware or a combination of these. The invention can be implemented by means of hardware comprising several distinct elements, by a dedicated processor, or by a general-purpose processor which is suitably programmed. Accordingly, another aspect of the invention provides software comprising instructions (code) which, when executed by a computer or processor, implement the method. The software may be tangibly embodied on an electronic memory device, hard disk, optical disk or any other machine-readable storage medium or it may be downloaded to the computer or processor via a network connection.

Further aspects of the invention provide a processor which is operable to perform the method and a system incorporating the processor. The system can take the form of a fixed or portable apparatus. Applications of the apparatus include detection of illicit substances by law-enforcement agencies.

BRIEF DESCRIPTION OF THE DRAWINGS

Embodiments of the invention will be described, by way of example only, with reference to accompanying drawings in which.

DETAILED DESCRIPTION OF THE DRAWINGS

This invention is based on the use of kernel methods for both the classification of materials or chemicals and the quantification of properties of materials or chemicals based on spectral data. This description reflects a single embodiment of the invention in which two particular standard kernels, the Linear and Radial Basis Function (RBF) kernel, are adapted. However, other standard kernels could be substituted without affecting the claims of the invention. This description refers to the use of a kernel-based learner; this is a generic term encompassing multiple different machine learning methods such as Support Vector Machines and Nearest Neighbour algorithms, which use are kernel-based. Any such kernel-based learner may be employed with this invention without affecting the claims of the invention.

A spectrum can be defined as a plot of quantities characterizing electromagnetic radiation (absorbance, transmittance, radiant power, energy, energy density, intensity, exitance, radiance, irradiance, etc.) plotted against wavelength, frequency or wavenumber. Wavenumber defines the number of waves per unit length and is inversely proportional to wavelength (and therefore directly proportional to frequency). The unit of wavenumber is $cm^{-1}$. In the context of this invention a spectrum comprises a sequence of intensity values, each recorded at a different frequency. In the case of Raman spectroscopy, the spectrum records the intensity versus the wavenumber of the light scattered from a sample. In the following description of this invention, each frequency (or wavenumber) is referred to as a spectral attribute and the intensity (or other quantity) recorded at a particular frequency in a spectrum is referred to as a spectral attribute value. Therefore, the spectral attribute value i of a spectrum refers to the intensity recorded at the $i^{th}$ frequency in that spectrum. Each spectral sample is described by a sequence of m spectral attribute values. It is assumed that the same set of spectral attributes (i.e. frequencies) is used for all spectra of a dataset.

Figure 1:
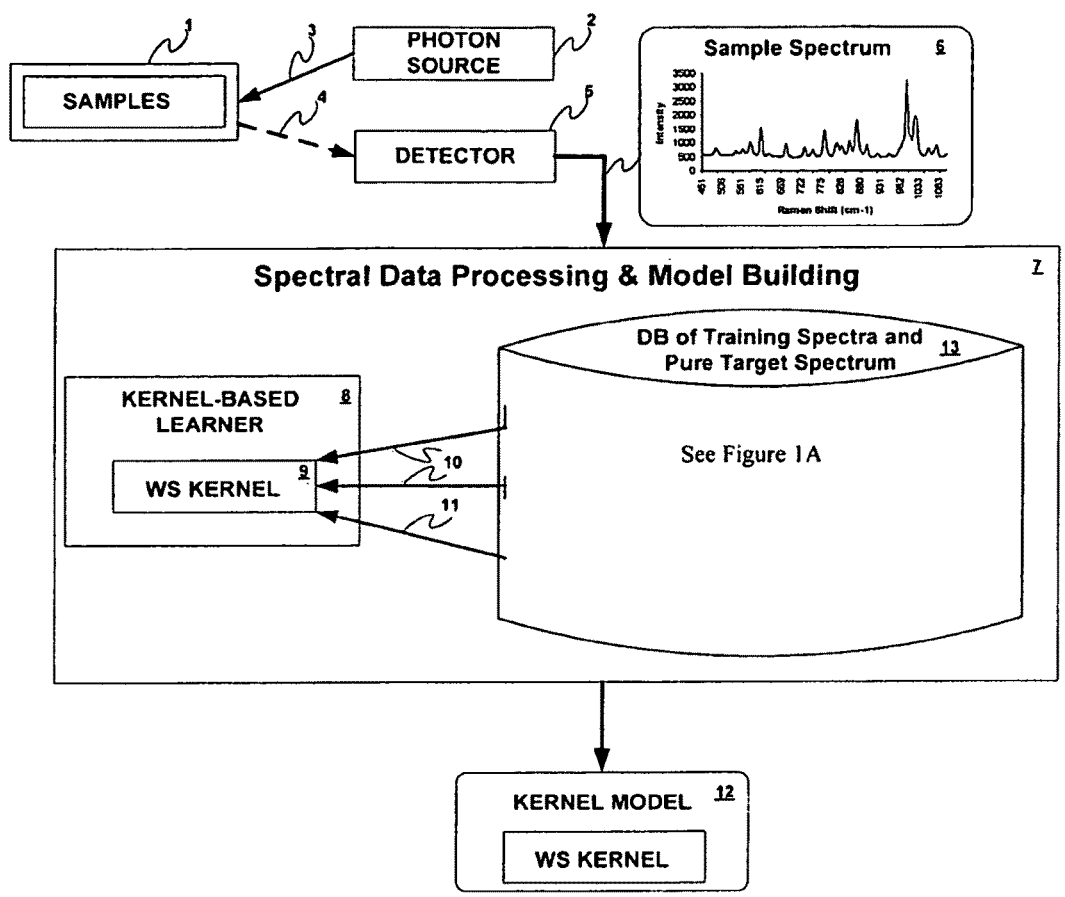
FIG. 1 schematically shows a system for analysing materials or chemicals to produce a prediction model in accordance with an embodiment of the invention.
Figure 1A:
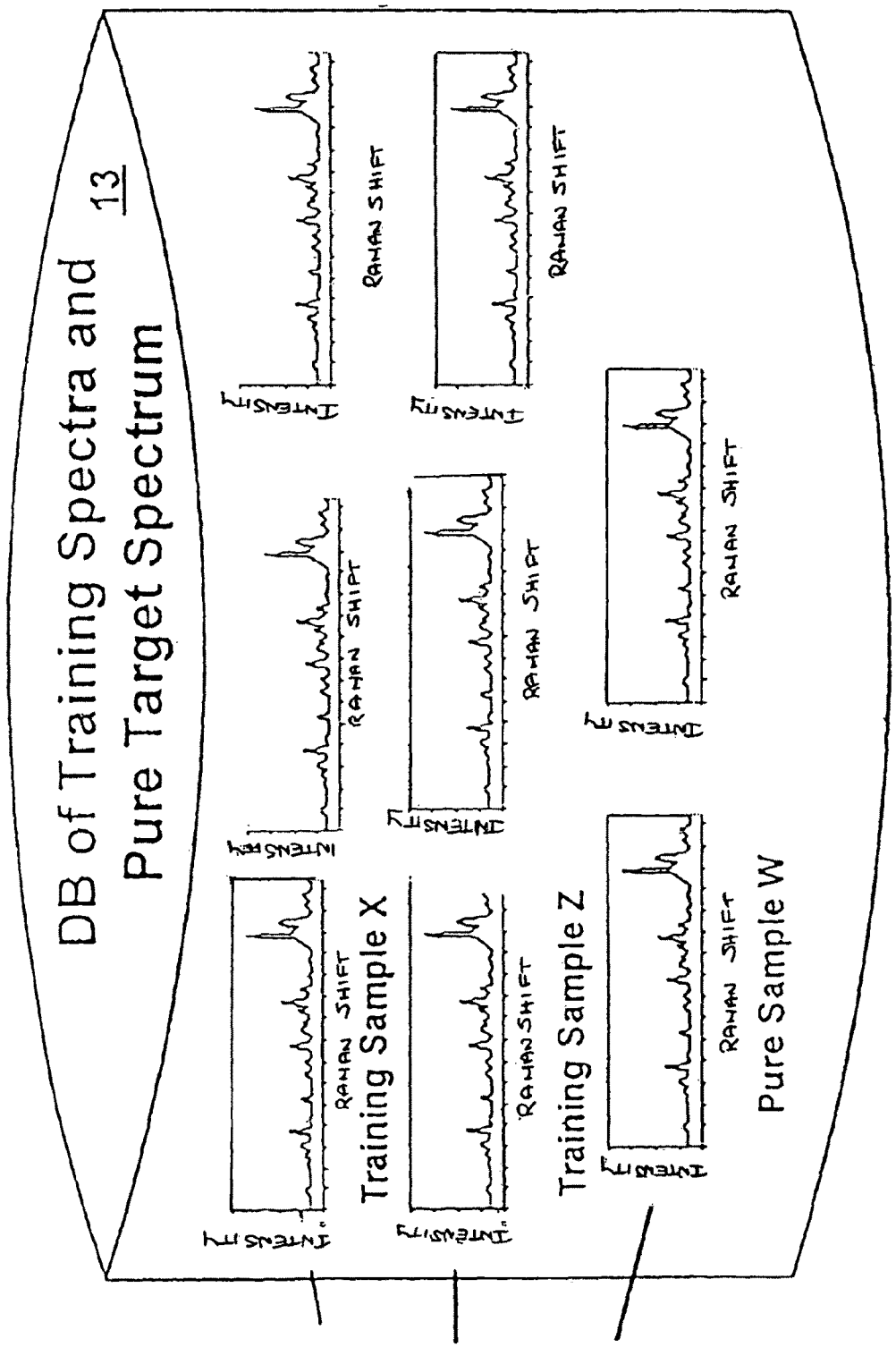

FIG. 1 schematically shows a system in accordance with an embodiment of the present invention. The purpose of the system is to build a model to be used for the future classification/quantification of an unknown material or chemical. A set of sample mixtures of known composition is first collected (1). A photon source (2) emits a beam of electromagnetic radiation (3), which is directed towards each sample. As a result of the interaction of the radiation and the sample, the characteristics of the radiation is changed (4) and this is detected by a detector (5), which outputs a spectrum for each sample mixture (6). Each spectrum comprises a range of spectral attribute values. For example, in Raman spectroscopy, the intensity values could be recorded over the range 0-4000 $cm^{-1}$. The spectral data is applied to a spectral data processing unit (7). This invention uses a kernel-based learner (8), e.g. the SVM (which is particularly advantageous as it is well suited to high-dimensional spectral data). The kernel-based learner uses the spectral database (13) to build a prediction model (12), which can be used for the quantification or classification of unknown mixtures (see FIG. 2). In the process of building this prediction model, the kernel-based learner uses the WS kernel (9) to calculate the similarity of pairs of sample spectra (10) from the spectral database. In the computation of these similarity measures, the WS kernel also uses the spectrum of the pure analyte (11), where the pure analyte is the material that is to be identified/quantified in unknown sample mixtures. Different embodiments of this invention incorporate different kernel-based learners (8), e.g. SVM and k-NN.

Figure 2:
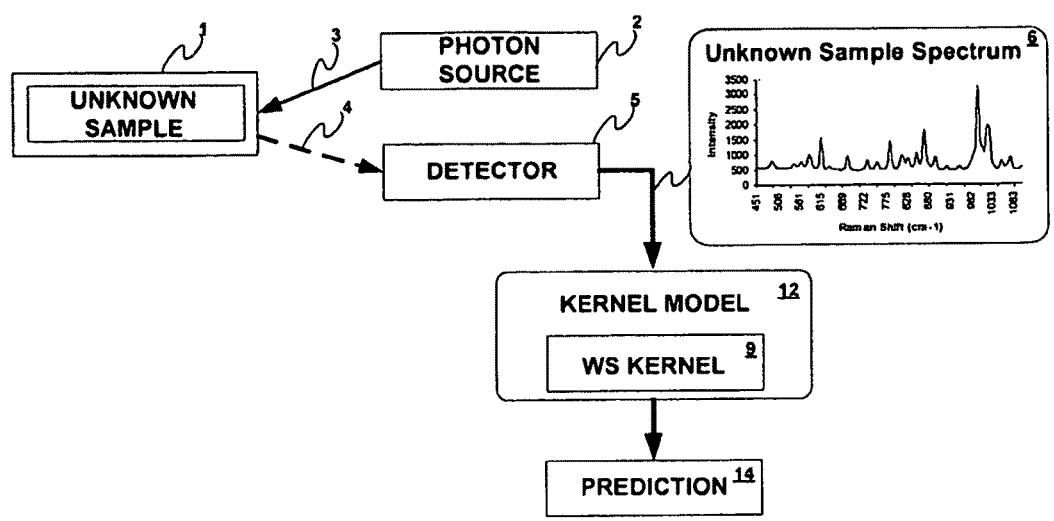
FIG. 2 schematically shows a system for analysing an unknown material or chemical to produce a prediction (classification or quantification) in accordance with an embodiment of the invention.

FIG. 2 shows a system in accordance with an embodiment of the present invention. The purpose of this system is to classify an unknown sample (1) of a chemical or material, which can be in the form of a solid, liquid or gas. A photon source (2) emits a beam of electromagnetic radiation (3), which is directed towards each sample. As a result of the interaction of the radiation and the sample, the characteristics of the radiation is changed (4) and this is detected by a detector (5), which outputs a spectrum for the unknown sample (6). This spectrum comprises a range of spectral attribute values. The unknown sample spectrum is then classified or quantified (14) by a kernel model (12), the model being produced by the system illustrated in FIG. 1 and incorporating a WS Kernel (9). Again, different embodiments of this invention use different kernel methods to general the kernel model used in the prediction step.

A kernel compares two spectral samples, x and z, as inputs and outputs a single value reflecting how similar they are to each other. A kernel typically compares two spectra by comparing the corresponding spectral attribute values and then combining these m attribute-based comparisons (e.g. by summing them) into a single measure of the similarity of sample x and sample z. In order to understand the improvements of the present invention, it is useful to first consider the operation of the standard Linear kernel:

1. Calculate the product of the first spectral attribute value of sample x and the first spectral attribute value of sample z.
2. Repeat Step 1 for each of the m spectral attributes.
3. Calculate the sum of these m products and return this as the similarity of sample x to sample z.

Figure 3:
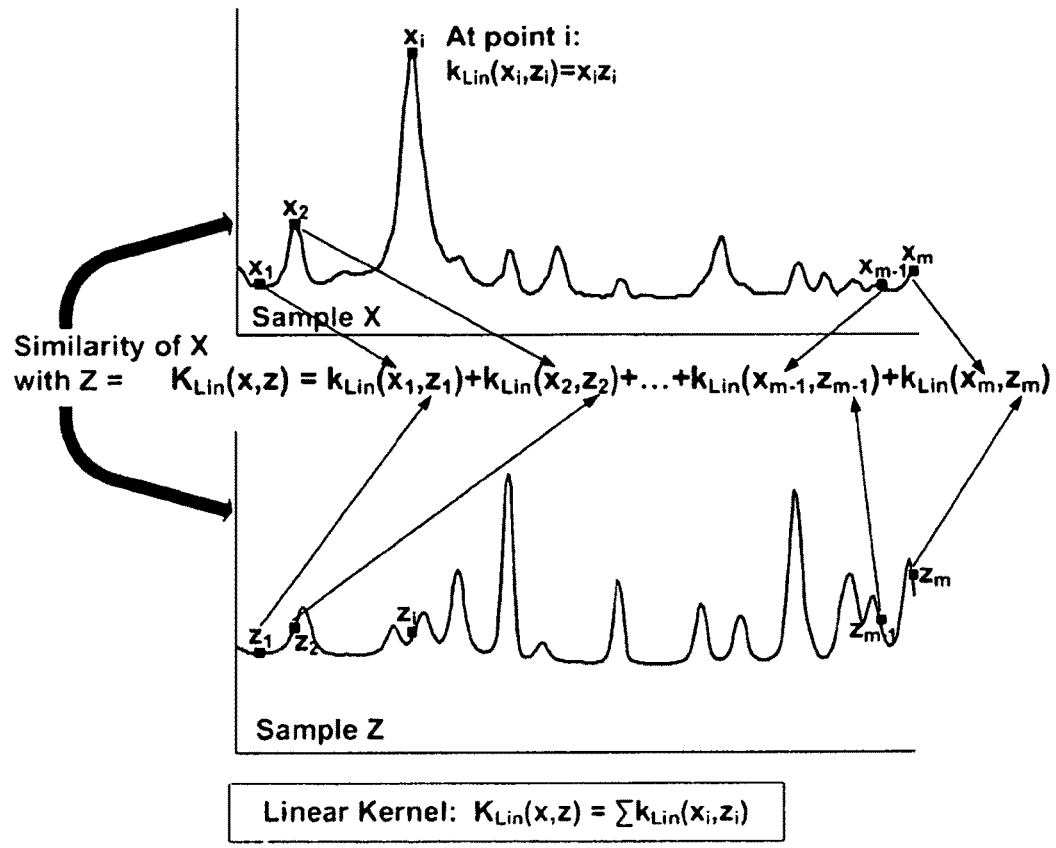
FIG. 3 is a schematic representation showing how two spectra are compared using a conventional Linear kernel.

The above process can be summarised as follows:

$$K_{Lin}(x, z) = \sum_{i=1}^{m} k_{Lin}(x_i, z_i)$$

where $k_{Lin}(x_i, z_i) = x_i z_i$ and $x_i$ and $z_i$ are the ith attribute values of sample x and z, respectively. This Linear kernel similarity measure is also illustrated in FIG. 3.

This invention applies two distinct modifications to the similarity measure of spectra as calculated by the Linear kernel. With the first modification, which will be called the Spectral Kernel, the similarity of two spectra, x and z, is calculated as follows:

1. Calculate the product of the first spectral attribute value of sample x and the first spectral attribute value of sample z.
2. Calculate the difference between the first spectral attribute value of sample x and the value of a number of its neighbouring spectral attributes (within a window of size 2W+1), to produce a set of 2W difference values. Different window sizes may be specified depending on the application.
3. Calculate the difference between the first spectral attribute value of sample z and the value of a number of its neighbouring spectral attributes (within a window of size 2W+1), to produce a set of 2W difference values.
4. Multiply and sum the set of differences generated from Steps 2 and 3, and add this value to the product generated in Step 1. This provides a single value for the comparison of the first attribute of sample x and sample z.
5. Repeat Steps 1 to 4 for the m spectral attributes.
6. Calculate the sum of the m values generated by all iterations of Steps 1 to 4 and return this as the similarity of sample x to sample z.

The above procedure can be summarised as follows:

$$K_{SLin}(x, z) = \sum_{i=1}^{m} k_{SLin}(x_i, z_i)$$

Figure 4:
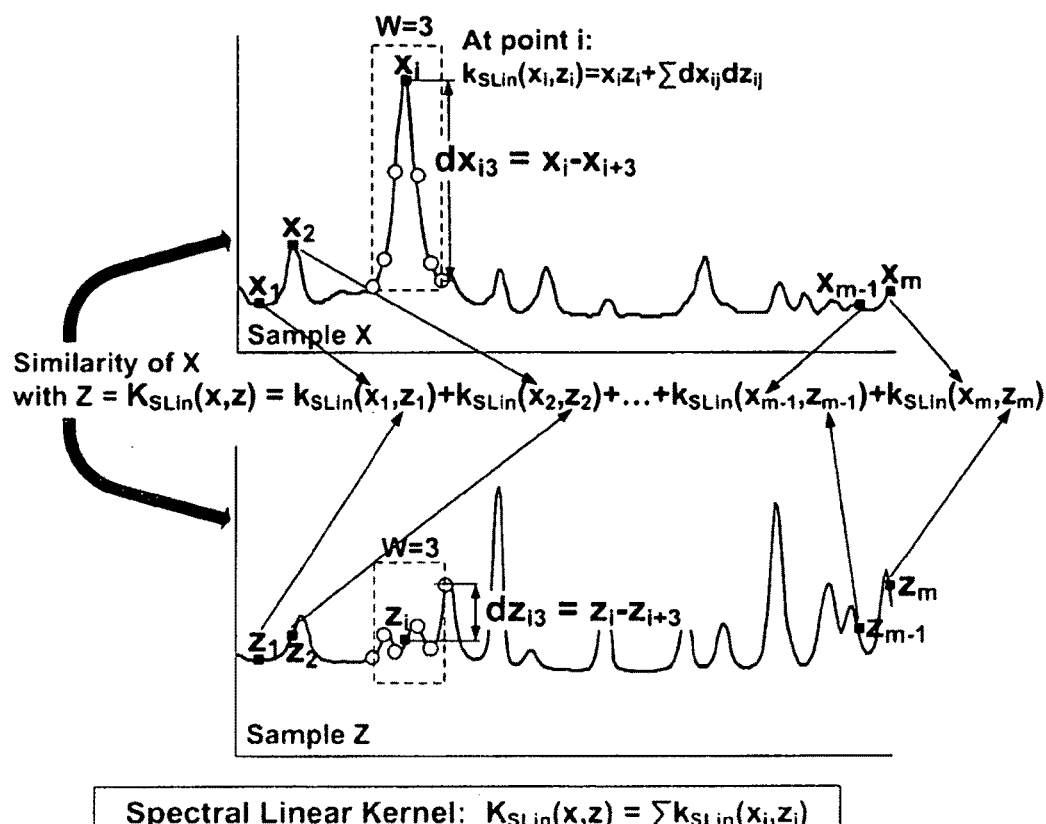
FIG. 4 is a schematic representation showing how two spectra are compared using the Spectral Linear kernel of the present invention.

-continued $$k_{SLin}(x_i, z_i) = x_i z_i + \sum_{j=i-W}^{i+W} \frac{(x_i - x_j)(z_i - z_j)}{dx_{ij} \quad dz_{ij}}$$

where $dx_{ij}$ is the set of differences generated by comparing the $i^{th}$ spectral attribute value of sample x with its neighbouring spectral attributes, and where $dz_{ij}$ is the set of differences generated by comparing the $i^{th}$ spectral attribute value of sample z with its neighbouring points. The Spectral Linear kernel similarity measure is also illustrated in FIG. 4. Through the use of local differences, this similarity is being incorporated with knowledge of the spectral profile of the two spectra, rather than just treating these spectral points in isolation. FIG. 4 shows the spectral linear kernel operating on the same pair of spectra as shown in the Linear kernel diagram of FIG. 3. In this example, W=3 (therefore a window size of 7) so that, when the kernel operates on point $x_i$, three points on either side of the selected point $x_i$ are considered. The effect of this improvement can be seen in FIG. 4. In sample X, point $x_i$ is positioned at the crest of a peak in the spectral response. The points immediately neighbouring point x, are located on the sides of the peak about point $x_i$. However, in sample Z, point $z_i$ is positioned within a series of troughs. The points immediately neighbouring point $z_i$ follow the rise-and-fall of the response on each side of point $z_i$. By basing the calculation of the kernel function at $x_i$ on the neighbouring W points on each side of $x_i$ as well as on the value of $x_i$ it can be seen that when a match does occur it will have a higher degree of confidence. This is particularly true if one considers an example where $x_i$ and $z_i$ each have the same intensity value, but where these spectral points are located within different features (e.g. $x_i$ on a peak and $z_i$ in a trough). In experiments, the window size is typically varied from 5 to 30. Experiments have also shown that choosing too large a window size (e.g. over 200) can result in an overly complex (as well as more computationally intensive) kernel that does not perform as well (in terms of prediction accuracy) as kernels based on smaller window sizes. The window (W) shown in FIG. 4 is symmetrical about the point $x_i$ and is the preferred form of the window. However, the window need not be symmetrical and in certain circumstances, such as when operating on points $x_i$ at each end of the spectrum, the window will have an asymmetric form.

In the second modification of the standard Linear kernel, which will be called the Weighted Spectral Kernel (WS Kernel), the spectrum of a pure analyte is used to incorporate a weighting scheme into the similarity measure. The pure analyte spectrum is referred to as sample w in the following description. The similarity of two spectra, x and z, using this WSLinear kernel is calculated as follows:

1. Normalise sample w so that all spectral attribute values lie in the range of 0 to 1. N*ote* that the samples x and z may also have been *normalised*, which does not *affect* the operation of this *invention*.
2. Calculate the product of the first spectral attribute value of sample x, the first spectral attribute value of sample z and the first spectral attribute value of sample w.
3. Calculate the difference between the first spectral attribute value of sample x and the value of a number of its neighbouring spectral attributes (within a window of size 2W+1), to produce a set of 2W difference values.
4. Calculate the difference between the first spectral attribute value of sample z and the value of a number of its neighbouring spectral attributes (within a window of size 2W+1), to produce a set of 2W difference values.

5. Calculate the difference between the first spectral attribute value of sample w and the value of a number of its neighbouring spectral attributes (within a window of size 2W+1), to produce a set of 2W difference values.
6. Multiply and sum the three set of differences generated from Steps 3-5 and add this value to the product generated in Step 1. The result of this calculation is multiplied by the first spectral attribute value of sample w. This generates a single value for the comparison of the first spectral attribute of sample x and sample z.
7. Repeat Steps 2 to 6 for the m spectral attributes.
8. Calculate the sum of the m values generated by all iterations of Steps 2 to 6 and return this as the similarity of sample x to sample z.

Figure 5:
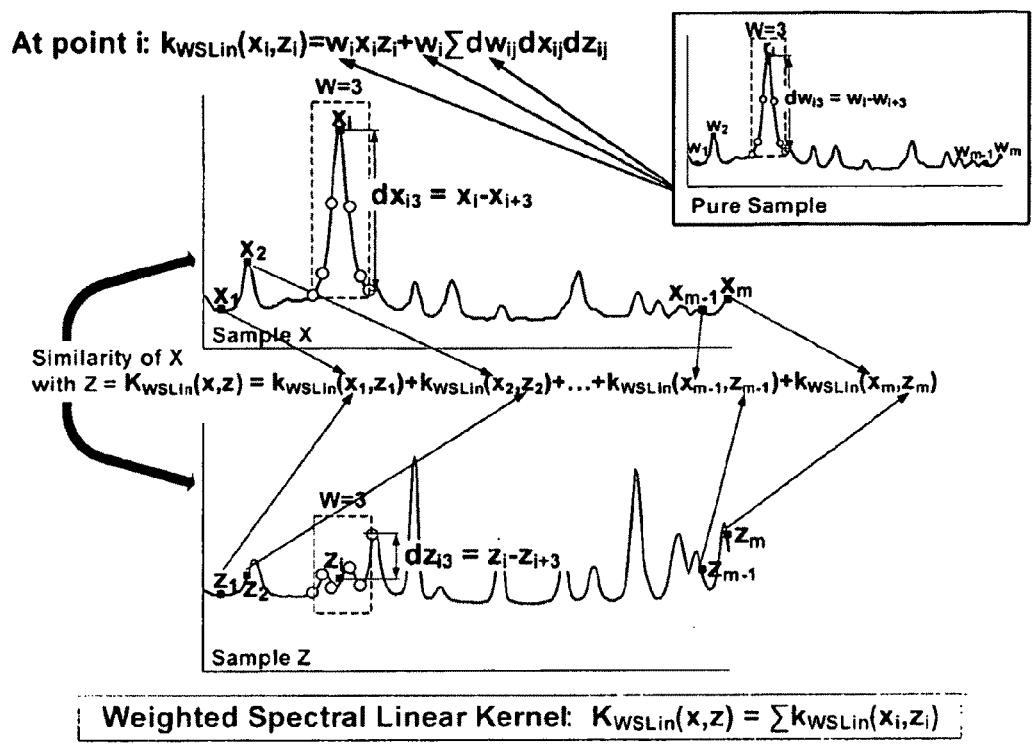
FIG. 5 is a schematic representation showing how two spectra are compared using the Weighted Spectral Linear kernel of the present invention.

The above procedure can be summarised as follows:

$$K_{WSLin}(x, z) = \sum_{i=1}^{m} k_{WSLin}(x_i, z_i)$$

$$k_{WSLin}(x_i, z_i) = w_i x_i z_i + w_i \sum_{j=i-W}^{i+W} \frac{(w_i - w_j)(x_i - x_j)(z_i - z_j)}{dw_{ij} \; dx_{ij} \; dz_{ij}}$$

where $dw_{ij}$ is the set of differences generated by comparing the $i^{th}$ spectral attribute value of the pure analyte spectrum, w, with value of its neighbouring spectral attributes. The WSLinear kernel similarity measure is also illustrated in FIG. 5. As can be seen from the above description and the illustration of FIG. 5, there are two elements to the weighting scheme used in the WSLinear kernel. The weight vector w is a set of values ranging from 0 to 1, based on the intensities recorded for the pure analyte spectrum. In this way, more importance is attached to those regions of the spectrum where peaks occur in the pure analyte spectrum. Similarly, the set of weights represented by $dw_{ij}$ is generated by calculating the differences for the attribute i (by comparing it with the surrounding attributes within a window) in the pure spectrum, and using this set of values to weight each product in the sum. As a result, the WSLinear kernel similarity measure will attach more importance to those differences between neighbouring spectral attributes of the two spectra being compared, where these same spectral attributes realise a substantial difference in the pure analyte spectrum. With this weighting scheme, the kernel is being incorporated with knowledge of the analyte. In effect, the WSLinear kernel represents a similarity measure for spectra that compares sample spectra in terms of the pure analyte. Therefore, similarities between spectra in regions that are not prominent in the original analyte spectrum are not considered as important as similarities occurring in regions where the pure analyte has a peak in its signal.

A similar modification can be made to the standard Radial Base Function (RBF) kernel, to give a Weighted Spectral Radial Base Function (WSRBF) kernel, in which the Euclidean distance calculation is modified (the new distance is denoted $d_{WS}(x,z)$). The details of the procedure for comparing two spectra using the WSRBF kernel similarity measure are not given, but can be summarised as follows:

$$K_{WSRBF}(x, z) = \exp\left(\frac{-d_{WS}(x, z)^2}{2\sigma^2}\right)$$

$$d_{WS}(x, z)^2 =$$

-continued $$w_i \sum_{i=1}^{m} (x_i - z_i)^2 + \sum_{i=1}^{m} w_i \sum_{j=i-W}^{i+W} \frac{(w_i - w_j)}{dw_{ij}} \left(\frac{(x_i - x_j)}{dx_{ij}} - \frac{(z_i - z_j)}{dz_{ij}}\right)^2$$

The two sets of weights, $w_i$ and $dw_{ij}$ are identical to those used for the WSLinear kernel and are generated in an identical fashion. As with the WSLinear kernel, the WSRBF kernel represents a similarity measure that is specific to spectral data and each variation of the kernel is designed for the classification or quantification of a particular analyte.

As mentioned, this invention can be applied to other standard kernels. For example, the application of the WS Kernel approach to the Polynomial kernel (WSPoly) can be expressed in terms of the WSLinear kernel as follows:

$$K_{WSPoly}(x, z) = \left(\sum_{i=1}^{m} k_{WSLin}(x_i, z_i) + 1\right)^d$$

where d is the degree of the WSPoly kernel.

The next four sections detail how this invention is used in different spectral analysis applications.

Classification of Materials or Chemicals Using WS Kernel Approach

Spectra are classified as follows:
1. A training dataset comprising the spectra of samples of known composition is collected.
2. The spectrum of the analyte in its pure form is collected (pure analyte spectrum).
3. An implementation of a kernel-based classification technique incorporating a WS kernel (e.g. WSLinear or WSRBF) is trained on the above dataset to produce a classification model. Parameters of both the kernel method and WS kernel may be tuned to achieve the best model of the training data. For example, in using an SVM classifier with the WSLinear kernel, the SVM C parameter and the WSLinear window size parameter could be optimised.
4. In the SVM example, the resultant SVM classification model is used to classify the unknown sample spectrum. The SVM decision process involves using the WS kernel to compare the unknown sample with one or more samples of the training dataset. Each comparison uses the pure analyte spectrum to weight the calculations.

The above method can be used with any kernel-based classification technique, and is not limited to use with a SVM.

WS Kernel Distance Metric for Spectra

In spectral analysis, it is common to compare the spectrum of an unknown material or chemical with a database of spectra of known materials and chemicals in order to identify a material or chemical. This involves the use of a distance measure to rank the spectra in order of similarity to the unknown material or chemical. The Euclidean distance measure, which calculates the distance between the two samples in the original input space, is often used for this type of search. A WS kernel can be used to derive a distance measure for use in spectral search. Using the kernel, K, the distance between two spectra, x and z, is defined as follows:

$$d_K(x,z) = \sqrt{K(x,x) + K(z,z) - 2K(x,z)}$$

The procedure for calculating the distance between two spectra using a WS kernel is as follows:
1. A training dataset comprised of the spectra of samples of known composition is collected.

2. The spectrum of the analyte in its pure form is collected (pure analyte spectrum).
3. A number of classification or regression models using a kernel-based method that incorporates a WS kernel. The different models are generated by changing parameters of the WS kernel, e.g. the window size parameter of a WSLinear kernel or the window size and σ parameter of a WSRBF kernel.
4. The WS kernel settings that achieved the best accuracy (classification or regression) on the training dataset are selected;
5. Using the selected kernel, K, the following kernel calculations are made: K(x,x), K(z,z) and K(x,z), where x is the first spectrum and z is the second spectrum.
6. The distance between the two spectra is given by the above expression for $d_K(x,z)$.

Quantification of Materials or Chemicals Using WS Kernel Approach

This invention can be used for the quantification of a property of a material or chemical using the spectra from the material or chemical, e.g. the measurement of the concentration of an analyte in a mixture based on the Raman spectrum of the mixture. The properties of materials or chemicals are quantified as follows:
1. A training dataset comprised of the spectra of samples in which the desired properties (e.g. concentration) of each sample are known.
2. The spectrum of the analyte in its pure form is collected (pure analyte spectrum).
3. An implementation of a kernel-based regression technique incorporating a WS kernel (e.g. WSLinear or WSRBF) is trained on the above dataset to produce a regression model. Parameters of both the kernel method and WS kernel may be tuned to achieve the best model of the training data. For example, in using SVM regression with the WSLinear kernel, the SVM C parameter and the WSLinear window size parameter could be optimised.
4. The resultant SVM regression model is used to quantify a property of the unknown sample spectrum. The SVM decision process involves using the WS kernel to compare the unknown sample with one or more samples of the training dataset.

This invention can also be used in the same way with any kernel-based regression technique, and is not limited to use with a SVM.

Visualisation of a Spectral Dataset Using the WS Kernel Approach

Two forms of visualisations are provided: one based on a classification model that incorporates a WS kernel and the other based on a regression model that incorporates a WS kernel. The visualisation is a two- or three-dimensional plot of the spectra of a dataset. It can be used by experts to discern patterns in a dataset, such as clusters of similar samples and outliers. A visualisation is generated as follows:
1. A training dataset comprising the spectra of samples of known composition is collected.
2. The spectrum of the analyte in its pure form is collected (pure analyte spectrum).
3. A number of classification or regression models using a kernel-based method that incorporates a WS kernel. The different models are generated by changing parameters of the WS kernel, e.g. the window size parameter of a WSLinear kernel or the window size and σ parameter of a WSRBF kernel.
4. The WS kernel settings that achieved the best accuracy (classification or regression) on the training dataset are selected. A kernel matrix, K, is constructed using this kernel setting, where a each element of the matrix, $K_{ij}$, is the similarity of sample i to sample j, as calculated by the selected WS kernel.
5. A MDS technique is used to transform the kernel matrix into a low-dimensional projection. An example of two MDS techniques that could be used are:
   a. Kernel PCA
   b. Laplacian Matrix method
6. The projections produced by the MDS technique are plotted on a graph. In a classification application, the points of the plot are coloured to indicate whether they are analyte-containing samples or not. In a quantification application, the points of the plot are coloured to indicate the property value of the analyte in each sample, e.g. in the prediction of concentration amounts, the colours can represent the 0-100% concentration range.

Figure 6:
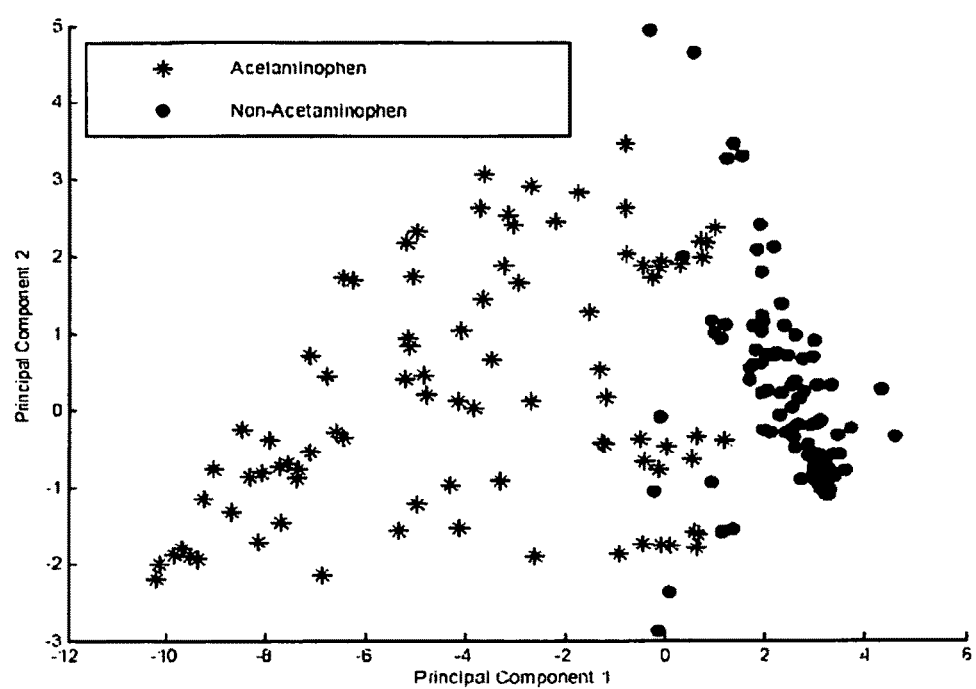
FIG. 6 is a visualisation of an acetaminophen dataset using a Weighted Spectral Linear kernel and kernel PCA.
Figure 7:
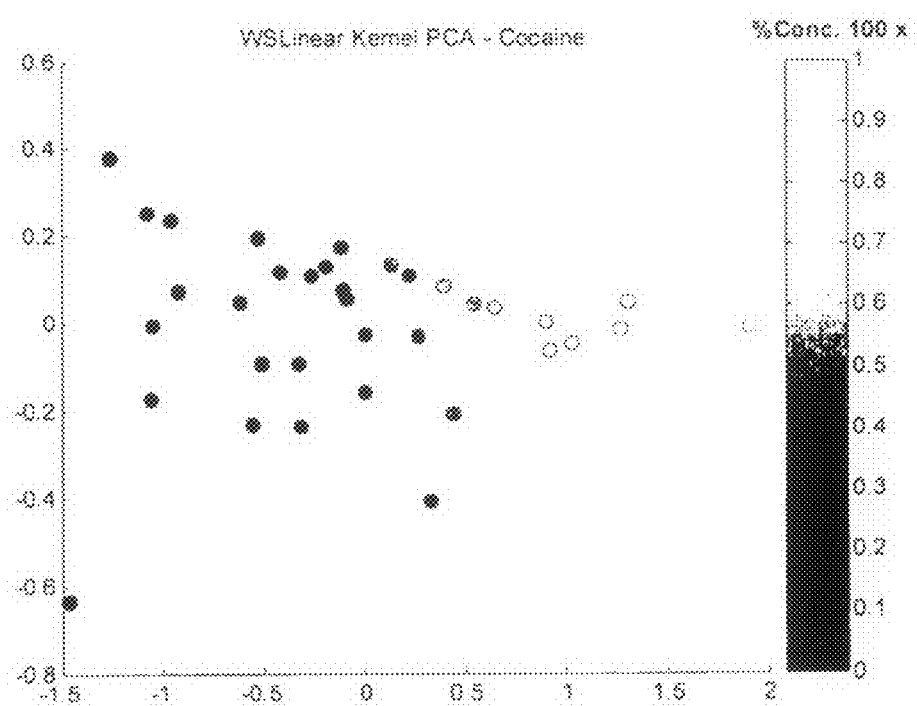
FIG. 7 is a visualisation of a cocaine dataset using a WSLinear kernel and kernel PCA.

Note that this visualisation procedure could be used with any MDS technique other than the two mentioned above. Furthermore, any kernel-based classification or regression technique may be used in the kernel selection step. A sample visualisation of a dataset is shown in FIG. 6. This visualisation shows the projection of a dataset, using kernel PCA based on a WSLinear kernel. This dataset is used to build a classification model for identifying acetaminophen samples. The dataset clearly shows a separation (with a small amount of overlap) between samples containing acetaminophen and those without acetaminophen. Another visualisation is shown in FIG. 7, which is also generated using kernel PCA with a WSLinear kernel. This visualisation shows a dataset collected for building a regression model to be used for quantifying cocaine in samples (i.e. the property being quantified is the cocaine concentration of each mixture). FIG. 7 demonstrates a good degree of correlation between a sample's cocaine concentration and its position in the graph; the cocaine concentration of the samples increases from left to right in the graph.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The invention claimed is:
1. A method of determining the similarity of a first spectrum and a second spectrum, each spectrum representing a result of spectral analysis of a material or chemical, each spectrum comprising a set of m spectral attributes distributed across a spectral range, the method comprising calculating a kernel function which comprises:
   (a) calculating the similarity of the two spectra at an $i^{th}$ one of the spectral attributes;
   (b) repeating the step of calculating for each of the set of m spectral attributes;
   (c) deriving a combined value indicative of the similarity of the two spectra wherein deriving the combined value includes adding the results of the m calculations,
   wherein calculating the similarity of the two spectra at the $i^{th}$ one of the spectral attributes comprises:
      determining a first difference between a value of the $i^{th}$ spectral attribute in the first spectrum and each of a set of neighboring spectral attributes within a first window around the $i^{th}$ spectral attribute in the first spectrum;

determining a second difference between a value of the $i^{th}$ spectral attribute in the second spectrum and each of a set of neighboring spectral attributes within a second window around the $i^{th}$ spectral attribute in the second spectrum, wherein the first and second windows are the same size.

2. A method according to claim 1 wherein each of the first and second windows comprises at least one other spectral attribute.

3. A method according to claim 1 wherein each of the first and second windows is symmetrical about the $i^{th}$ spectral attribute.

4. A method according to claim 1 wherein calculating the similarity of the two spectra at the $i^{th}$ one of the spectral attributes further comprises:

combining the first and second differences to obtain a combined difference;

multiplying the value of the $i^{th}$ spectral attribute in the first spectrum by the valve of the $i^{th}$ spectral attribute in the second spectrum, and adding the combined difference to the result of the multiplying step.

5. A method according to claim 1 wherein the similarity produced by the calculating step is further based on multiplying the first difference by the second difference and summing each pair of first and second differences.

6. A method according to claim 1, wherein the step of calculating the similarity comprises:

applying a weighting value to the calculated similarity, wherein deriving the combined value further includes negating the sum obtained by the adding the results of the m calculations, dividing the negated sum by a quantity, and calculating the exponential of the divided negated sum.

7. A method according to claim 6 wherein there is a third spectrum comprising a set of m spectral attributes distributed across the spectral range, the third spectrum representing a target analyte, and the similarity value at step (a) is further based on:

calculating the difference between the value of the $i^{th}$ spectral attribute in the third spectrum and each of a set of neighboring spectral attributes within a window around the $i^{th}$ spectral attribute in the third spectrum and using each of the calculated differences for the third spectrum as the weighting value.

8. A method according to claim 6 wherein the similarity of step (a) is further calculated by:

subtracting the first difference for the second spectrum from the first difference for the first spectrum, squaring the result and multiplying this squared result by the first difference in the third spectrum;

repeating the subtracting step for each difference within the window;

adding the results produced by each subtracting iteration; and multiplying the added results by the value of the $i^{th}$ spectral attribute in the third spectrum to obtain a multiplied final sum.

9. A method according to claim 8, further comprising multiplying the squared result by the value of $i^{th}$ spectral attribute in the third spectrum.

10. A method according to claim 8 wherein step (a) further comprises squaring the difference between the value of the $i^{th}$ spectral attribute in the first and second spectra and adding the output of the squaring and the output of the multiplied final sum.

11. A method according to claim 1, wherein the step of calculating the similarity comprises: applying a weighting value to the calculated similarity value.

12. A method according to claim 1 wherein a weighting value is applied to each of the first and second differences.

13. A method according to claim 1 wherein there is a third spectrum comprising a set of m spectral attributes distributed across the spectral range, the third spectrum representing a target analyte, and the calculated value is further based on:

calculating a third difference between the value of the $i^{th}$ spectral attribute in the third spectrum and each of a set of neighboring spectral attributes within a window around the $i^{th}$ spectral attribute in the third spectrum and using each of the calculated differences for the third spectrum as a weighting value.

14. A method according to claim 13 wherein the calculated similarity is based on:

multiplying the first difference by the second and third differences for the $i^{th}$ spectral attribute within the window;

summing the results of the set of difference calculations;

multiplying the summed result by the $i^{th}$ spectral attribute in the third spectrum.

15. A method according to claim 14 further comprising multiplying the $i^{th}$ spectral attribute in the first spectrum by the $i^{th}$ spectral attribute in the second spectrum and by the $i^{th}$ spectral attribute in the third spectrum.

16. A method according to claim 14 wherein the calculating the similarity further comprises multiplying the value of the $i^{th}$ spectral attribute in the first spectrum with the valve of the $i^{th}$ spectral attribute in the second spectrum and adding same to the multiplied summed result of claim 15.

17. A method according claim 11 further comprising normalising the third spectrum so that all of the spectral attributes of the third spectrum lie in the range of 0 to 1.

18. A method according to claim 1, further comprising classifying unknown compounds based on their spectra, wherein classifying unknown compounds includes the steps of:

providing a training set of training spectra, each spectrum representing a mixture of known compounds and each having a plurality of spectral attributes distributed across a spectral range;

using a kernel-based classification or regression technique, which uses the kernel function to compare pairs of the training spectra, to build a prediction model based on the training set;

using the prediction model to classify an unknown sample by using the kernel function to compare a spectrum of the unknown sample with one or more training spectra.

19. A method according to claim 1, further comprising quantifying the properties of unknown compounds based on their spectra, wherein quantifying the properties includes the steps of:

providing a training set of training spectra, each spectrum representing a mixture of known compounds and each having a plurality of spectral attributes distributed across a spectral range;

using a kernel-based classification or regression technique, which uses the kernel function to compare pairs of training spectra, to build a prediction model based on the training set;

using the prediction model to determine a property of an analyte in an unknown sample by using the kernel function to compare a spectrum of the unknown sample with one or more training spectra.

20. A method according to claim 1, further comprising calculating the distance between two spectra wherein calculating the distance includes the steps of:
    providing a training set of training spectra, each spectrum representing a mixture of known compounds and each having a plurality of spectral attributes distributed across a spectral range;
    using a kernel-based classification or regression technique, which uses the kernel function to compare pairs of training spectra, to build a prediction model based on the training set;
    selecting the kernel that resulted in a prediction model of the best accuracy on the training set;
    using the selected kernel to calculate the distance between the two spectra.

21. A method according to claim 1, further comprising generating a visualisation of a spectral dataset wherein generating the visualization includes the steps of:
    providing a training set of training spectra, each spectrum representing a mixture of known compounds and each having a plurality of spectral attributes distributed across a spectral range;
    using a kernel-based classification or regression technique, which incorporates a kernel function to compare two training spectra, to build a number of prediction models based on the training set;
    selecting the kernel that resulted in a prediction model of the best accuracy on the training set;
    calculating a kernel matrix, K, for the training dataset where each element of the matrix, $K_{ij}$, is the kernel similarity measure for spectrum i and j and K comprises the similarity measure for all pairs of samples in the training dataset;
    using a Multi-Dimensional Scaling (MDS) technique to transform the kernel matrix into a two- or three-dimensional projection;
    plotting the MDS projection on a graph, where each point of the graph represents a sample spectrum of the original training set.

22. A method according to claim 21 wherein the plotting of the graph comprises colouring each point of the graph to either:
    highlight the target-containing samples of the training dataset from the non-target containing samples by using a different colour for points from the two groups; or,
    indicate the concentration of the analyte in each sample by using a graded colour scheme for the points corresponding to a 0-100% range in concentration amounts.

23. A method according to claim 20 wherein calculating the distance between two spectra comprises the steps of:
    (a) calculating K(x,x), where K is a Kernel function and x is the first spectrum;
    (b) calculating K(z,z), where K is a Kernel function and z is the second spectrum;
    (c) calculating K(x,z), where K is a Kernel function, x is the first spectrum and z is the second spectrum;
    (d) adding the output of step (a) to the output of step (b), subtracting double the output of step (c) from this sum, and calculating the square root of the result.

24. A system for classifying or quantifying spectra comprising:
    a storage device for storing at least a first spectrum and a second spectrum, each spectrum representing a result of spectral analysis of a material or chemical, each spectrum comprising a set of m spectral attributes distributed across a spectral range; and,
    a processor operable to calculate a plurality of similarities of the two spectra at each of an $i^{th}$ one of the spectral attributes; and
    combine the plurality of similarities to obtain a combined value indicative of the similarity of the two spectra, wherein
    for each $i^{th}$ one of the spectral attributes, the corresponding similarity is based on a comparison of the value of the $i^{th}$ spectral attribute in the first spectrum and each of a set of neighboring spectral attributes within a window around the $i^{th}$ spectral attribute in the first spectrum,
    for each $i^{th}$ one of the spectral attributes, the corresponding similarity is based on a comparison of the value of the $i^{th}$ spectral attribute in the second spectrum and each of a set of neighboring spectral attributes within a window around the $i^{th}$ spectral attribute in the second spectrum, and
    the windows in the first and second spectrum are the same size.

25. A system according to claim 24 further comprising: a photon source and a detector for performing spectral analysis of a sample.

26. A non-transitory computer-readable medium carrying instructions which, when executed by a processor, cause the processor to perform the method according to a method for determining the similarity of a first spectrum and a second spectrum, each spectrum representing a result of spectral analysis of a material or chemical, each spectrum comprising a set of m spectral attributes distributed across a spectral range, the method comprising calculating a kernel function which comprises:
    calculating a plurality of similarities of the two spectra at an $i^{th}$ one of the m spectral attributes;
    combing the plurality of similarities to derive a value indicative of the similarity of the two spectra, wherein
    calculating each similarity of the two spectra at an $i^{th}$ attribute comprises:
        determining a first difference between the value of the $i^{th}$ spectral attribute in the first spectrum and each of a set of neighboring spectral attributes within a first window around the $i^{th}$ spectral attribute in the first spectrum;
        determining a second difference between the value of the $i^{th}$ spectral attribute in the second spectrum and each of a set of neighboring spectral attributes within a second window around the $i^{th}$ spectral attribute in the second spectrum, and
        wherein the first and second windows are the same size.

* * * * *